(12) United States Patent
Nocker et al.

(10) Patent No.: US 10,605,743 B2
(45) Date of Patent: Mar. 31, 2020

(54) METHOD FOR MAINTAINING MECHANICAL APPARATUS BASED ON ANALYTICS OF SURFACE PHOTOGRAPHIES

(71) Applicant: Siemens Aktiengesellschaft, Munich (DE)

(72) Inventors: Gerhard Nocker, Shanghai (CN); Bjoern Engels, Shanghai (CN)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/328,779

(22) PCT Filed: Aug. 30, 2017

(86) PCT No.: PCT/CN2017/099751
§ 371 (c)(1),
(2) Date: Feb. 27, 2019

(87) PCT Pub. No.: WO2018/041156
PCT Pub. Date: Mar. 8, 2018

(65) Prior Publication Data
US 2019/0226998 A1   Jul. 25, 2019

(30) Foreign Application Priority Data

Aug. 31, 2016 (CN) .......................... 2016 1 0797410

(51) Int. Cl.
   *G01N 21/88*   (2006.01)
(52) U.S. Cl.
   CPC ......... *G01N 21/8806* (2013.01); *G01N 21/88* (2013.01); *G01N 21/8851* (2013.01);
   (Continued)

(58) Field of Classification Search
   CPC .......... G01N 21/8806; G01N 21/8851; G01N 21/9501; G03N 21/8803
   (Continued)

(56) References Cited

U.S. PATENT DOCUMENTS 5,461,417 A   10/1995   White et al.
5,684,530 A   11/1997   White
(Continued)

FOREIGN PATENT DOCUMENTS

CN   101726498 A   6/2010
CN   102481668 A   5/2012
(Continued)

OTHER PUBLICATIONS

International Search Report PCT/ISA/210 for International Application No. PCT/CN2017/099751 dated Nov. 30, 2017.
(Continued)

*Primary Examiner* — Hung Nguyen
(74) *Attorney, Agent, or Firm* — Harness, Dickey & Pierce, P.L.C.

(57) ABSTRACT

Disclosed is a method for maintaining a mechanical apparatus, with the surface of a component thereof being damaged. In an embodiment, the method includes: taking at least one photograph for at least one component; processing the photograph to obtain geometric data of the component; comparing the data with a predetermined standard; and indicating the component meeting the predetermined standard.

17 Claims, 3 Drawing Sheets

Figure 1:
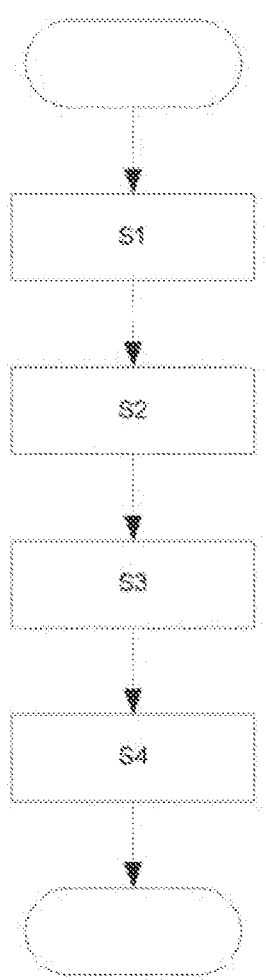

(52) U.S. Cl.
CPC ............ *G01N 2021/8861* (2013.01); *G01N 2021/8887* (2013.01)

(58) Field of Classification Search
USPC ........................................ 356/145
See application file for complete search history.

(56) References Cited

U.S. PATENT DOCUMENTS

| | | | |
|---|---|---|---|
| 8,996,156 B2 | 3/2015 | Melzer-Jokisch et al. | |
| 9,310,312 B2* | 4/2016 | Jahnke | G01N 21/8851 |
| 9,719,774 B2 | 8/2017 | Ullrich et al. | |
| 2007/0165211 A1* | 7/2007 | Ishikawa | G01N 21/95607 356/145 |
| 2011/0254946 A1* | 10/2011 | Fukazawa | G01N 21/9501 348/128 |
| 2012/0179285 A1 | 7/2012 | Melzer-Jokisch et al. | |
| 2012/0297600 A1 | 11/2012 | Ullrich et al. | |
| 2013/0163849 A1 | 6/2013 | Jahnke et al. | |
| 2014/0315330 A1* | 10/2014 | Fujimori | G03F 7/70641 438/7 |
| 2015/0057952 A1 | 2/2015 | Coombs et al. | |

FOREIGN PATENT DOCUMENTS

| | | |
|---|---|---|
| CN | 103052877 A | 4/2013 |
| CN | 203299134 U | 11/2013 |
| CN | 103562712 A | 2/2014 |
| CN | 104422696 A | 3/2015 |
| WO | WO-9419908 A1 | 9/1994 |

OTHER PUBLICATIONS

Written Opinion of the International Searching Authority PCT/ISA/237 for International Application No. PCT/CN2017/099751 dated Nov. 30, 2017.

\* cited by examiner

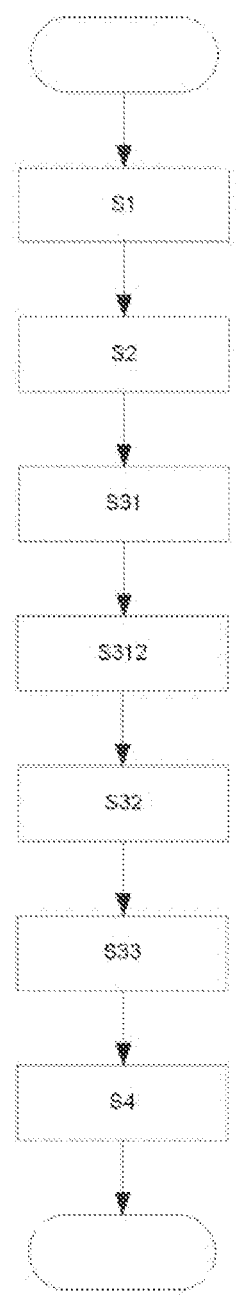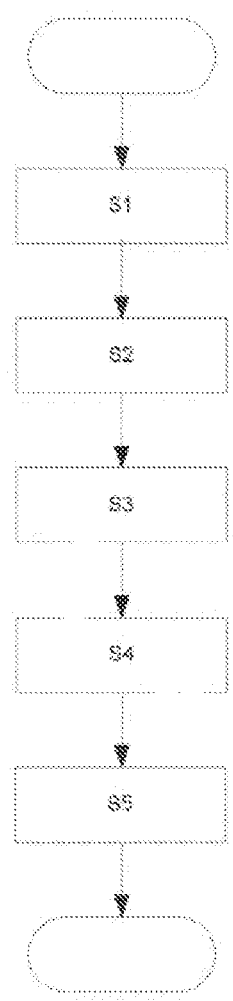
Figure 3                    Figure 4

METHOD FOR MAINTAINING MECHANICAL APPARATUS BASED ON ANALYTICS OF SURFACE PHOTOGRAPHIES

PRIORITY STATEMENT

This application is the national phase under 35 U.S.C. § 371 of PCT International Application No. PCT/CN2017/099751 which has an International filing date of Aug. 30, 2017, which designated the United States of America and which claims priority to Chinese patent application number CN 201610797410.2 filed Aug. 31, 2016, the entire contents of which are hereby incorporated herein by reference.

FIELD

At least one embodiment of the invention generally relates to a method for maintaining mechanical equipment, particularly mechanical equipment with surface damages on its components or parts. Such mechanical equipment may be a combustion gas turbine, steam turbine, wind generator, compressor, etc.

BACKGROUND

The surfaces of the components and parts will be damaged after the mechanical equipment has been running for some time. Such damages may be wear and tear in the material or surface cracks on the components or parts. To assure a reliable operation of the mechanical equipment, it is necessary to deal with these damages in a timely manner by, for example, replacing the damaged parts with new ones. In the case of combustion gas turbines, one of the most frequent maintenance jobs is to use new ceramic insulating tiles to replace old ones that have cracks and/or wear and tear in the material. Usually, this job needs to shut down the gas turbine first before the ceramic insulating tiles are checked one by one visually by a specially trained engineer to assess which tiles need to be replaced based on the location and length of cracks or the amount of material loss.

The existing approach stated in the above has the following disadvantages: first, the inspections can only be performed manually by a specialist; second, the specialist's visual inspections are time-consuming and arduous, and occasionally human errors can happen, which will affect the reliable operation of the gas turbine.

SUMMARY

A purpose of at least one embodiment of the invention is to provide a method for maintaining mechanical equipment with surface damages on its components or parts, which can reduce the difficulty in maintaining the mechanical equipment with surface damages on its components or parts, improve its work efficiency, save the physical energy of the operators, and avoid human errors.

In an embodiment, the method includes:
S1: Take at least one photo for at least one component or part;
S2: Process the photo to acquire the geometric data of the component or part;
S3: Compare the data with the predetermined criteria;
S4: Give relevant instructions to the component or part which reaches the predetermined criteria.

In an embodiment, a method is disclosed for maintaining mechanical equipment with surface damages on at least one component or part of the mechanical equipment, the method comprising:
taking at least one photo of the at least one component or part;
processing the at least one photo to acquire geometric data of the at least one component or part;
comparing the geometric data acquired with criteria; and
giving relevant instructions to the at least one component or part to reach the criteria.

BRIEF DESCRIPTION OF ACCOMPANYING DRAWINGS

The accompanying drawings below are for example illustration, embodiments and explanation of the invention only, and do not limit the scope of the invention.

Figure 2:
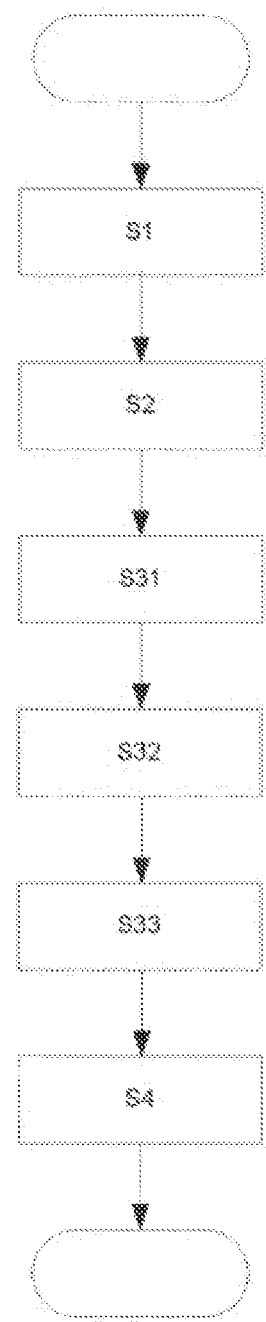
Figure 5:
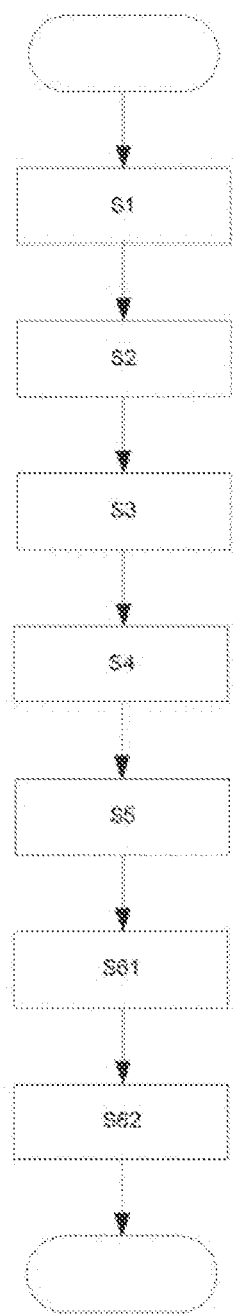
Figure 6:
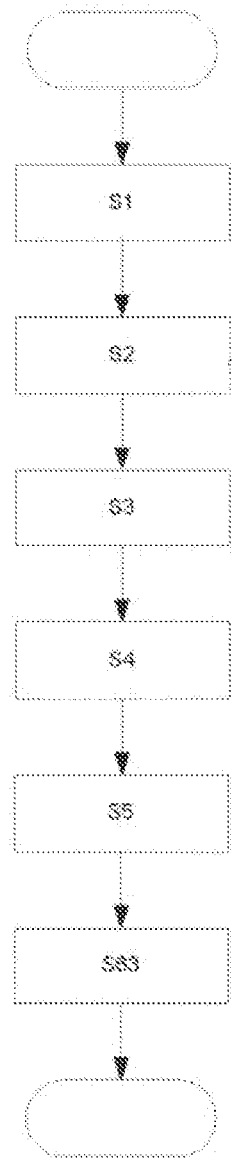

FIG. 1 presents an example flow diagram of the method for maintaining mechanical equipment with surface damages on its components or parts according to the first embodiment of the invention;

FIG. 2 presents an example flow diagram of a method for maintaining mechanical equipment with surface damages on its components or parts according to the second embodiment of the invention;

FIG. 3 presents an example flow diagram of a method for maintaining mechanical equipment with surface damages on its components or parts according to the third embodiment of the invention;

FIG. 4 presents an example flow diagram of a method for maintaining mechanical equipment with surface damages on its components or parts according to the fourth embodiment of the invention;

FIG. 5 presents an example flow diagram of a method for maintaining mechanical equipment with surface damages on its components or parts according to the fifth embodiment of the invention;

FIG. 6 presents an example flow diagram of a method for maintaining mechanical equipment with surface damages on its components or parts according to the sixth embodiment of the invention.

DETAILED DESCRIPTION OF EXAMPLE EMBODIMENTS

In an embodiment, the method includes:
S1: Take at least one photo for at least one component or part;
S2: Process the photo to acquire the geometric data of the component or part;
S3: Compare the data with the predetermined criteria;
S4: Give relevant instructions to the component or part which reaches the predetermined criteria.

One embodiment of the method for maintaining mechanical equipment with surface damages on its components or parts according to the invention is that, the step S3 includes, in turn, the following steps:
S31: Compare the data with the geometric features of various components or parts to identify the types of the component or part;
S32: Compare the data with the location and length of cracks allowed for the component or part.

Wherein, the step S31 helps to find the predetermined criteria corresponding to the components or parts more easily and quickly.

Another embodiment of the method for maintaining mechanical equipment with surface damages on its components or parts according to this invention is that, after the step S31, the method further includes a step S33: Compare the data with the standard geometrical shape of the component or part to calculate the material loss.

Another embodiment of the method for maintaining mechanical equipment with surface damages on its components or parts according to this invention is that, after the step S31 and before the step S32, the method further includes a step S312: Identify the location of the component or part in the mechanical equipment. This step further specifies more specific and detailed predetermined criteria corresponding to the component or part and helps the operator to easily locate the component or part to be replaced.

Another embodiment of the method for maintaining mechanical equipment with surface damages on its components or parts according to this invention is that, in the step S312, the location of the component or part in the mechanical equipment may be identified by scanning the marks on the component or part.

Another embodiment of the method for maintaining mechanical equipment with surface damages on its components or parts according to this invention is that, in the step S312, the location of the component or part in the mechanical equipment may be identified by comparing the data with the geometric features of the component or part.

Another embodiment of the method for maintaining mechanical equipment with surface damages on its components or parts according to this invention is that, after the step S4, the method further includes a step S5: Send the data to a server. This step allows the related data to be processed remotely.

Another embodiment of the method for maintaining mechanical equipment with surface damages on its components or parts according to this invention is that the step S1, step S2, step S3, and step S4 are implemented by an evaluating and measuring device.

Another embodiment of the method for maintaining mechanical equipment with surface damages on its components or parts according to this invention is that the evaluating and measuring device is mobile electronic equipment.

Another embodiment of the method for maintaining mechanical equipment with surface damages on its components or parts according to this invention is that in the step S1, the photo is taken by one or more cameras, and in the step S2, step S3 and step S4, the photo is processed, the data are compared with the predetermined criteria, and the component or part that reaches the predetermined criteria is indicated, all of which are performed by mobile electronic equipment.

Another embodiment of the method for maintaining mechanical equipment with surface damages on its components or parts according to the invention is that the mobile electronic equipment is a smart phone or tablet.

Another embodiment of the method for maintaining mechanical equipment with surface damages on its components or parts according to the invention is that the camera is a stereo camera or a camera lens.

Another embodiment of the method for maintaining mechanical equipment with surface damages on its components or parts according to the invention is that, after the step S5, the method further includes a step S61: Analyze the data on the server.

Another embodiment of the method for maintaining mechanical equipment with surface damages on its components or parts according to this invention is that, after the step S61, the method further includes a step S62: Update the predetermined criteria. This step helps to ensure that maintenance of the mechanical equipment is always based on the latest development results through creating and updating new criteria for component and part replacement.

Another embodiment of the method for maintaining mechanical equipment with surface damages on its components or parts according to this invention is that, after the step S5, the method further includes a step S63: Provide quotation or clarification for replacement parts. This step provides convenience to users, further improves the maintenance efficiency, and saves even more time.

To understand more clearly the technical characteristics, purposes and effects of the invention, specific embodiments of this invention are hereby explained by referring to the accompanying drawings. The same reference numbers in the drawings stand for the same part.

As used herein, the word "example" means "serving as an example, instance, or illustration." Thus, any "example" graphical representation and embodiment described herein shall not be construed to be a preferred or advantageous technical plan.

As used herein, the words "a or an" may mean "only this one" and may also mean "more than one".

FIG. 1 presents an example flow diagram of the method for maintaining mechanical equipment with surface damages on its components or parts according to the first embodiment of this invention. This method includes, in turn, the following steps:

S1: Take at least one photo for at least one component or part;

S2: Process the photo to acquire the geometric data of the component or part;

S3: Compare the data with the predetermined criteria;

S4: Give relevant instructions to the component or part which reaches the predetermined criteria.

The method of an embodiment of the invention is used to maintain mechanical equipment with surface damages on its components or parts, where cracks and/or wear and tear in material may occur due to surface damages of the components or parts. In this application, cracks include both cracks in material and holes or pits of various shapes as long as they are visible on the surface of the components or parts. The mechanical equipment can be a combustion gas turbine, steam turbine, wind generator, compressor, etc., while the components or parts can be ceramic insulating tiles, stator blades, rotor blades, bearings, shells, train wheels, etc. The method of this invention can reduce the difficulty in maintaining the mechanical equipment with surface damages on its components or parts, improve the work efficiency, save the physical energy of the operators, and avoid human errors.

Also take as an example the ceramic insulating tile (component or part) of a combustion gas turbine, which can be photographed by the operator. As long as the operator is capable of taking clear photos with a camera, there is no need to train the operator. The camera can be a regular camera, a stereo camera or a camera lens. While photos can be either digital or film version. After that, a computer or a mobile electronic device such as smart phone or tablet is used as the evaluating and measuring device to process the digital photos to obtain the geometric data of the ceramic insulating tile, such as length, width, thickness and other dimensions, as well as the length, location and shape of cracks in it.

In the case of taking film photos, of course, the film photos need to be digitized and converted into digital photos in advance to carry out the step S2. The data obtained are further compared with the predetermined criteria stored in the evaluating and measuring device. When the related data reach the predetermined criteria, namely, the length, width, thickness and other dimensions of the ceramic insulating tile or the length, location and shape of the cracks in it, exceed the allowable ranges in design, it means that the continued use of this ceramic insulating tile may affect the reliable operation of the combustion gas turbine. At this time, the evaluating and measuring device indicates the ceramic tile to be replaced, such as through the computer monitor or directly on the screen of the smartphone or tablet.

Those skilled in the art will understand that the specific range allowed by the predetermined criteria will vary depending on the design and may be adjusted depending on specific circumstances. The step S1, step S2, step S3 and step S4 can be all implemented through the evaluating and measuring device, which can be a computer or a mobile electronic device such as a smartphone or tablet. The photos in the step S1 may be taken by one or more cameras, and, in the step S2, step S3 and step S4, the photo is processed, the data are compared with the predetermined criteria, the component or part reaching the predetermined criteria is indicated, all of which are performed by mobile electronic equipment used as the evaluating and measuring device. In the evaluating and measuring device, relevant software has been installed, such as application software in the smartphone or tablet. The software can process the photo according to a specific algorithm to obtain the geometric data of the component or part, compare the data with the predetermined criteria, and indicate the component or part that reaches the predetermined criteria.

FIG. 2 presents an example flow diagram of the method for maintaining mechanical equipment with surface damages on its components or parts according to the second embodiment of the invention. Its difference from the first embodiment is that, the step S3 further includes, in turn, the following steps:

s31: Compare the data with the geometric features of various components or parts to identify the type of the component or part;

S32: Compare the data with the location and length of cracks allowed for the component or part;

S33: Compare the data with the standard geometrical shape of the component or part to calculate the material loss.

The geometric features of a certain type of component or part refer to the common features in geometric shapes, which can be used to distinguish different types of components or parts, such as rotor blades and stator blades, or different types of rotor blades. The location and length of cracks allowed for a component or part can be the location of cracks that is allowed for that component or part. In case of any differences in the location and length of cracks allowed for the same parts at different locations, it refers to the location and length of cracks allowed for that specific part at that location.

The standard geometric shape of a component or part can be either the geometric shape designed for that type of component or part, or, if there are differences in the standard geometric shape of the same type of component or part for different locations, the geometric shape designed for the specific component or part at that location. In the inspection of different types of components or parts, the components or parts can be several types of ceramic insulating tiles, stator blades, and rotor blades of the combustion gas turbine.

Under the condition that the type of the component or part, such as ceramic insulating tile, is clear, the type of the component or part may be further subdivided into various ceramic tiles used by the combustion gas turbine. In this way, the predetermined criteria corresponding to the component or part can be found more easily and quickly by the evaluating and measuring device.

Those skilled in the art will understand that it is not necessary to include the step S33 after the step S32, or that cracks can be processed by the method of this invention only whereas wear and tear in material may be processed by another method. In case that the step S33 is used, that is, the wear and tear in material needs to be calculated, then the geometric data must be obtained through three-dimensional photos, and the sequence of the step S32 and step S33 can be exchanged. The three-dimensional photos can be obtained by a stereo camera, or by combining at least two two-dimensional photos taken from different angles by ordinary cameras, and the geometric data of surface cracks can be obtained simply through two-dimensional photos but can also be obtained through three-dimensional photos.

FIG. 3 presents an example flow diagram of the method for maintaining mechanical equipment with surface damages on its components or parts according to the third embodiment of the invention. Its difference from the first and second embodiments is that after the step S31 and before the step S32, the method further includes a step S312: Identify the location of the component or part in the mechanical equipment.

Identifying the location of the component or part in the mechanical equipment may help to further define the specific and detailed predetermined criteria corresponding to the component or part, and it is convenient for operators to locate the component or part that needs to be replaced. Also take as an example the combustion gas turbine's ceramic tiles, which are often arranged next to each other to form a single insulating layer. Therefore, all or several ceramic tiles may be included in one photo, and the evaluating and measuring device (such as a smartphone) can automatically identify the location of the ceramic tiles to be replaced.

This photo covering all or several ceramic tiles can be formed by combining several partial photos into a panoramic photo, and the combination operation can be done through the evaluating and measuring device. In the step S312, the location of the component or part in the mechanical equipment may be identified by scanning the mark on the component or part (i.e. the so-called optical character recognition, or OCR), or the location of the component or part in the mechanical equipment is identified by comparing the data with the geometric characteristics of the component or part.

FIG. 4 presents an example flow diagram of the method for maintaining mechanical equipment with surface damages on its components or parts according to the fourth embodiment of the invention. Its difference from the first to third embodiments is that after the step S4, the method further includes a step S5: Send the data to a server.

Although the evaluating and measuring devices, such as smartphone or tablet, can work independently, there are additional advantages if the related data can be remotely processed through a server. For example, the data loss can be prevented by uploading the related data to the cloud for storage.

FIG. 5 presents an example flow diagram of the method for maintaining mechanical equipment with surface damages on its components or parts according to the fifth embodiment of the invention. Its difference from the first to fourth embodiments is that after the step S5, the method further includes the following steps:

S61: Analyze the data on the server;

S62: Update the predetermined criteria.

Performing a big data analysis on the data in the server can bring the following benefits: Firstly, whether the damage prediction and the design criteria are correct can be known by collecting and analyzing data from different mechanical equipment of the same type, which makes it possible to extend the maintenance cycle and reduce the maintenance frequency. Secondly, a model can be established to predict the damage by combining the damage information of a large number of components or parts with the operation information of mechanical equipment (including load, temperature, vibration, and other information). Lastly, the manufacturer of the mechanical equipment can understand the replaced components or parts and update the as-built documents in a timely manner to fully and accurately know the current information of the mechanical equipment for subsequent operation and maintenance. Including the step S62 after the step S61 is not necessary but updating the predetermined criteria can ensure the maintenance of the mechanical equipment is always based on the latest development results by creating and updating the replacement criteria for the components or parts.

FIG. 6 presents an example flow diagram of the method for maintaining mechanical equipment with surface damages on its components or parts according to the sixth embodiment of the invention. Its difference from the first to fifth embodiments is that after the step S5, the method further includes a step S63: Provide quotation or clarification for replacement parts. Preferably, the quotation or clarification for a replacement part is performed automatically with a remote computer system through the server.

If the geometry data obtained by the evaluating and measuring device is of poor quality, or if the automatic evaluating and measuring has no or unclear results, the clarification may be conducted manually and remotely. In this case, the server can automatically trigger the process flow of a manufacturer's engineering department, and the corresponding engineer is responsible for answering the user's questions within a certain period of time and sending the results through the server to the evaluating and measuring device, such as a smartphone or tablet. A step of sending a report to the evaluating and measuring device through the server may be added after the maintenance is done. In addition, if the user accepts the manufacturer's offer, the user can also make purchases online through the software in the evaluating and measuring device. The manufacturer can promptly deliver the component or part to the user, which provides convenience to the user, further improves the maintenance efficiency, and saves even more time.

It should be understood that while the specification is described according to each embodiment, it is not necessary that one embodiment contains only one independent technical plan. The narrative description is only for the sake of clarity, those skilled in the art should see the specification, and the technical plans in the respective embodiments may be suitably combined to form other embodiments understandable by those skilled in the art.

The detailed description in the above is merely for describing the feasible embodiments of the present invention and does not intend to limit the scope of protection for the invention. Any equivalent embodiments or changes, such as combination, division, or repetition of features, which do not depart from the spirit of the present invention, should be included in the scope of protection for this invention.

The invention claimed is:

1. A method for maintaining mechanical equipment with surface damages on at least one component or part of the mechanical equipment, the method comprising:
   taking at least one photo of the at least one component or part;
   processing the at least one photo to acquire geometric data of the at least one component or part;
   comparing the geometric data acquired with criteria, the comparing including
      comparing the geometric data acquired with geometric features of various components or parts to identify types of the at least one component or part,
      comparing the geometric data acquired with a standard geometrical shape of the at least one component or part to calculate a material loss, and
      comparing the geometric data acquired with permissible location and length of cracks for the at least one component or part; and
   giving relevant instructions to the at least one component or part to reach the criteria.

2. The method of claim 1, wherein after the comparing of the geometric data acquired with the geometric features and before the comparing of the geometric data acquired with permissible location and length of cracks, the method further includes identifying the location of the at least one component or part in the mechanical equipment.

3. The method of claim 2, wherein, in the identifying, the location of the at least one component or part in the mechanical equipment is identifiable by scanning marks on the at least one component or part.

4. The method of claim 2, wherein, in the identifying, the location of the at least one component or part in the mechanical equipment is identifiable by comparing the data with the geometric features of the at least one component or part.

5. The method of claim 1, wherein, after the giving of the relevant instructions, the method further includes sending at least one of the relevant instructions and the geometric data acquired to a server.

6. The method of claim 5, wherein, the method is implemented by an evaluating and measuring device.

7. The method of claim 6, wherein the evaluating and measuring device includes mobile electronic equipment.

8. The method of claim 1, wherein, in the taking of the at least one photo, the photo is taken by one or more cameras, and in the processing, comparing and giving, all performed by mobile electronic equipment, the photo is processed, compared with the criteria, and the component or part that reaches the criteria is indicated.

9. The method of claim 7, wherein the mobile electronic equipment is a smart phone or tablet.

10. The method of claim 8, wherein the camera is a stereo camera or a camera lens.

11. The method of claim 5, wherein, after the sending, the method further includes analyzing the at least one of the relevant instructions and the geometric data acquired, on the server.

12. The method of claim 11, wherein, after the analyzing, the method further includes updating the criteria.

13. The method of claim 5, wherein after the sending, the method further includes providing a quotation or clarification for replacement parts.

14. The method of claim 5, wherein after the comparing of the geometric data acquired with the geometric features and before the comparing of the geometric data acquired with permissible location and length of cracks, the method further includes identifying the location of the at least one component or part in the mechanical equipment.

15. The method of claim 14, wherein, in the identifying, the location of the at least one component or part in the mechanical equipment is identifiable by scanning marks on the at least one component or part.

16. The method of claim 14, wherein, in the identifying, the location of the at least one component or part in the mechanical equipment is identifiable by comparing the data with the geometric features of the at least one component or part.

17. The method of claim 8, wherein the mobile electronic equipment is a smart phone or tablet.

* * * * *